US012279988B2

(12) United States Patent
Nelson et al.

(10) Patent No.: US 12,279,988 B2
(45) Date of Patent: Apr. 22, 2025

(54) SHOULDERED ARM SLING WITH SHOULDER SADDLE FOR ERGONOMICALLY AND COMFORTABLY DISSEMINATING THE WEIGHT OF THE SUPPORTED ARM DURING CONVALESCENCE

(71) Applicants: Preston G. Nelson, Mount Vernon, IL (US); George A Paletta, St. Louis, MO (US)

(72) Inventors: Preston G. Nelson, Mount Vernon, IL (US); George A Paletta, St. Louis, MO (US)

( * ) Notice: Subject to any disclaimer, the term of this patent is extended or adjusted under 35 U.S.C. 154(b) by 557 days.

(21) Appl. No.: 17/803,064

(22) Filed: Jan. 29, 2022

(65) Prior Publication Data

US 2022/0241103 A1 Aug. 4, 2022

Related U.S. Application Data

(63) Continuation-in-part of application No. 17/300,027, filed on Feb. 11, 2021, now abandoned.

(60) Provisional application No. 62/995,878, filed on Feb. 17, 2020.

(51) Int. Cl.
*A61F 5/37* (2006.01)
*A61F 5/40* (2006.01)

(52) U.S. Cl.
CPC .................................. *A61F 5/3738* (2013.01)

(58) Field of Classification Search
CPC .... A61F 5/3738; A61F 5/3746; A61F 5/3753; A61F 5/3723; A61F 5/3715; A61F 5/373; A61F 5/37; A61F 5/40
See application file for complete search history.

(56) References Cited

U.S. PATENT DOCUMENTS

| | | | | |
|---|---|---|---|---|
| 2,056,925 A | * | 10/1936 | Kimbrough | A47D 13/025 224/264 |
| 4,389,005 A | * | 6/1983 | Cable | A47D 13/025 224/159 |
| 4,446,858 A | * | 5/1984 | Verter | A61F 5/3738 602/20 |
| 5,203,482 A | * | 4/1993 | Puff | A45F 3/12 224/264 |

(Continued)

*Primary Examiner* — Camtu T Nguyen
(74) *Attorney, Agent, or Firm* — Sandberg Phoenix & von Gontard, P.C.

(57) ABSTRACT

A shouldered arm sling provided for treatment of various injuries to the arm, wrist, hand, of a patient, during convalescence, the sling includes primary straps and a saddle-style member, connecting with the front and back straps of the sling, the saddle-style member having a pair of straps, one strap rests upon the upper shoulder of the patient, the second strap rests upon the lateral side of the patient's shoulder, and the bifurcated straps have a flexible fabric type member connecting intermediately thereof, in order to provide for the dissemination of the generated forces on the shoulder from the weight of the arm being supported during its healing. The flexible fabric forms the saddle strap into a concaved configuration, to ergonomically fit upon the upper segment of the supporting shoulder, to add stability and comfort to the patient. A supplemental strap secures auxiliary to the primary straps, and prevents lateral shifting of the entire saddle when the supporting shoulder's arm is lifted above the head.

8 Claims, 6 Drawing Sheets

(56) References Cited

U.S. PATENT DOCUMENTS

| | | | | |
|---|---|---|---|---|
| 5,413,552 A | * | 5/1995 | Iwuala | A61F 5/3738 |
| | | | | 602/20 |
| 5,628,725 A | * | 5/1997 | Ostergard | A61F 5/3746 |
| | | | | 602/61 |
| 6,182,873 B1 | * | 2/2001 | Christopher | A47D 13/025 |
| | | | | 229/160 |
| 6,485,445 B1 | * | 11/2002 | Hiltner | A61F 5/373 |
| | | | | 128/845 |
| 2008/0119770 A1 | * | 5/2008 | Miller | A61F 5/3738 |
| | | | | 602/4 |
| 2017/0014259 A1 | * | 1/2017 | Quigley | A61F 5/3738 |

* cited by examiner

SHOULDERED ARM SLING WITH SHOULDER SADDLE FOR ERGONOMICALLY AND COMFORTABLY DISSEMINATING THE WEIGHT OF THE SUPPORTED ARM DURING CONVALESCENCE

CROSS-REFERENCE TO RELATED APPLICATION

This is a continuation-in-part patent application of the non-provisional patent application having Ser. No. 17/300,027, filed on Feb. 11, 2021, which latter application is a non-provisional of the provisional patent application having Ser. No. 62/995,878 which was filed on Feb. 17, 2020.

FIELD OF INVENTION

The concept of this invention is to provide a sling for supporting a broken arm during rehabilitation, and in order to disseminate the weight of the arm upon the region of the shoulder, where the strap of the sling locates, and a shoulder pad type of support bifurcated into two sections, with some supporting and resilient structure intermediate thereof, whereby the bifurcated strap extends over the upper outer region of the shoulder, and the second section around the side of the shoulder, and provides for that dissemination of the weight of the arm so as to reduce fatigue, prevent bruising and neck abrasion, and perhaps accelerate the healing of the wounded limb.

BACKGROUND OF THE INVENTION

The arm sling is one of the most prevalent orthotic devices used throughout the whole history of human orthopedic therapy, in order to stabilize and support the weight of an affected arm to facilitate rehabilitation to the injured upper extremity.

Traditional-style arm slings employ a single strap which secures to the affected limb and wraps up and over the other side of the user's torso, typically anchoring adjacent to the neck as it passes from the front to the back of the body. This causes unnatural stress and strain from the considerable force, especially in the vicinity of the neck, trapezius, clavicle and acromioclavicular joint. This often results in inconsistent use of the orthotic, affecting the duration of the care and success of rehabilitation, as well as the livelihood of the user for whatever time necessary during actual use of the device.

Instead of generating a regional pain in the neck, it is better to truly disseminate the weight of the affected limb on the shoulder (deltoid) of the stronger, healthy side. This was the partial goal of one prior invention. U.S. Pat. No. 10,512,516 to Quigley, et all (Arm Support), its downfall is that applied forces will still be limited to one narrow line. There is no method to usefully and reliably secure the perimeter of the force distribution portion, rendering it unstable and perhaps totally ineffective. In use, the single line across which its forces effectively fall will shift medially, further and further across the AC joint, onto the trapezius, and towards the neck, as the healthy arm is lifted in use, because there is no means to securely adhere the lateral perimeter to the lower deltoid. Furthermore, claim 8 of that patent even claims to apply force across the clavicle and trapezius, which our new invention seeks to totally relieve. Other prior inventions and patents such as U.S. Pat. No. 7,563,236 to Kazmierczak et al. (Shoulder Sling With Support Pillow And Pouch) and patent No. 8414512 to Fout (Shoulder Orthosis Shows a Supportive Strapping System) both sought to relieve the neck, the trapezius, and the clavicle of weight bearing, but appear to fall short of really "shouldering" the force, anchoring it directly over the AC joint. They feature a bifurcated ring, passing over the torso, probably no more laterally than the AC joint, and around the torso via the armpit. They provide no mechanism to further disseminate the supported forces laterally over all or even much of the deltoid muscle, as all of their attachments are medial of the humerus. Our new invention places supported forces over the top of the supper portion of the humerus, and around the far lateral side of it (the deltoid). These two prior inventions limit forces to the region of the AC joint, and to the armpit (pectoralis and teres muscles).

United States patent to Hubbard, et al, U.S. Pat. No. 4,372,301, shows a traditional shoulder strap for an arm sling. U.S. Pat. No. 4,716,895, to Marques, et al, shows another type of arm sling, and which would appear to have some padding at its upper segment. The patent to Clement, U.S. Pat. No. 5,403,268, shows another arm support, with supplemental straps provided for suspending its shoulder saddle. And, U.S. Pat. No. 10,179,075, to Hickling, upon a shoulder thermal therapy wrap, shows a strap means for holding a compression member against the shoulder being treated.

SUMMARY OF THE INVENTION

This disclosure generally concerns the use of upper extremity support devices, including arm slings.

Beneficial aspects of this arm sling with shoulder saddle include:

A secure fit via bifurcated straps to separately divide and support horizontal and lateral forces.

A comfortable fit by ergonomically anchoring the sling to the supporting shoulder with a concavely formed material there between the bifurcated strap saddle, hence limiting the applied forces to the deltoid area, and relieving the user's neck, trapezius, and clavicle of direct forceful weight.

A further object of this invention is to provide a structure means for a sling that disseminates the weight of the arm, where the strapped sling extends over the opposite shoulder, in order to relieve the isolated point force generally encountered by the injured party, during rehabilitation.

A further object of this invention is to provide for a separation of the strap of the sling that extends over the opposite shoulder during rehabilitation application, so that part of the force of the weight of the arm is upon the upper part of the shoulder's deltoid, and another part of that force will extend around the side of the shoulder during usage.

A further object of this invention is to provide for an intermediate support upon the strap of the sling that extends over the shoulder of the user during rehabilitation, and thereby disseminates the weight of the healing arm during its usage.

Another object of this invention is the provision of a short length of sleeve that is integrated with the arm sling and more particularly its shoulder supporting area, in order to prevent the sling from rising up on to the shoulder and neck of the wearer, during its continuous usage and application.

These and other objects may become more apparent to those skilled in the art upon review of the Summary of the Invention as provided herein, and upon undertaking a study of the Description of its Preferred Embodiment, in view of the Drawings.

DESCRIPTION OF THE PREFERRED EMBODIMENT

The concept of this invention is to provide a sling for supporting a broken arm during rehabilitation, and in order to disseminate the weight of the arm upon the region of the shoulder and deltoid, where the strap of the sling locates, and the shoulder pad type of support bifurcated into two sections, with some supporting structure intermediate thereof, whereby the bifurcated strap extends over the upper outer region of the shoulder, and the second section around the side of the shoulder, and provides for that dissemination of the weight of the injured arm so as to reduce fatigue, and perhaps accelerate the healing of the wounded limb.

As demonstrated in the figures, the bifurcated shoulder saddle strap system is designed so that one strap will rest on top of the user's supporting-side shoulder and carry a majority of the vertical forces from the user's injured and supported arm. In addition, the other strap will rest on the side of that same supporting-side shoulder and carry a majority of the lateral forces generating from the supporting arm, thus preventing the saddle from shifting medially towards the user's AC joint, clavicle, trapezius, and neck, which are weight sensitive and easily subject to irritation, due to the continuous carrying of the forces generated from the sling supported mending arm weight.

As weight from the injured arm pulls the sling system down, and medially, into and across the user's supporting shoulder, the bifurcated straps of the saddle system are held in place by a flexible intermediately located fabric, formed concavely by the shoulder inside of it. Thus, this results in further force dissemination and increased stability and security of usage. In addition, the individual straps may be further padded, in order to add to the comfort of its usage, and in addition, the intermediate flexible fabric, may be resilient, so that the straps may shift further apart, or closer together, depending upon the size of the supporting shoulder of the patient being treated.

Figure 1:
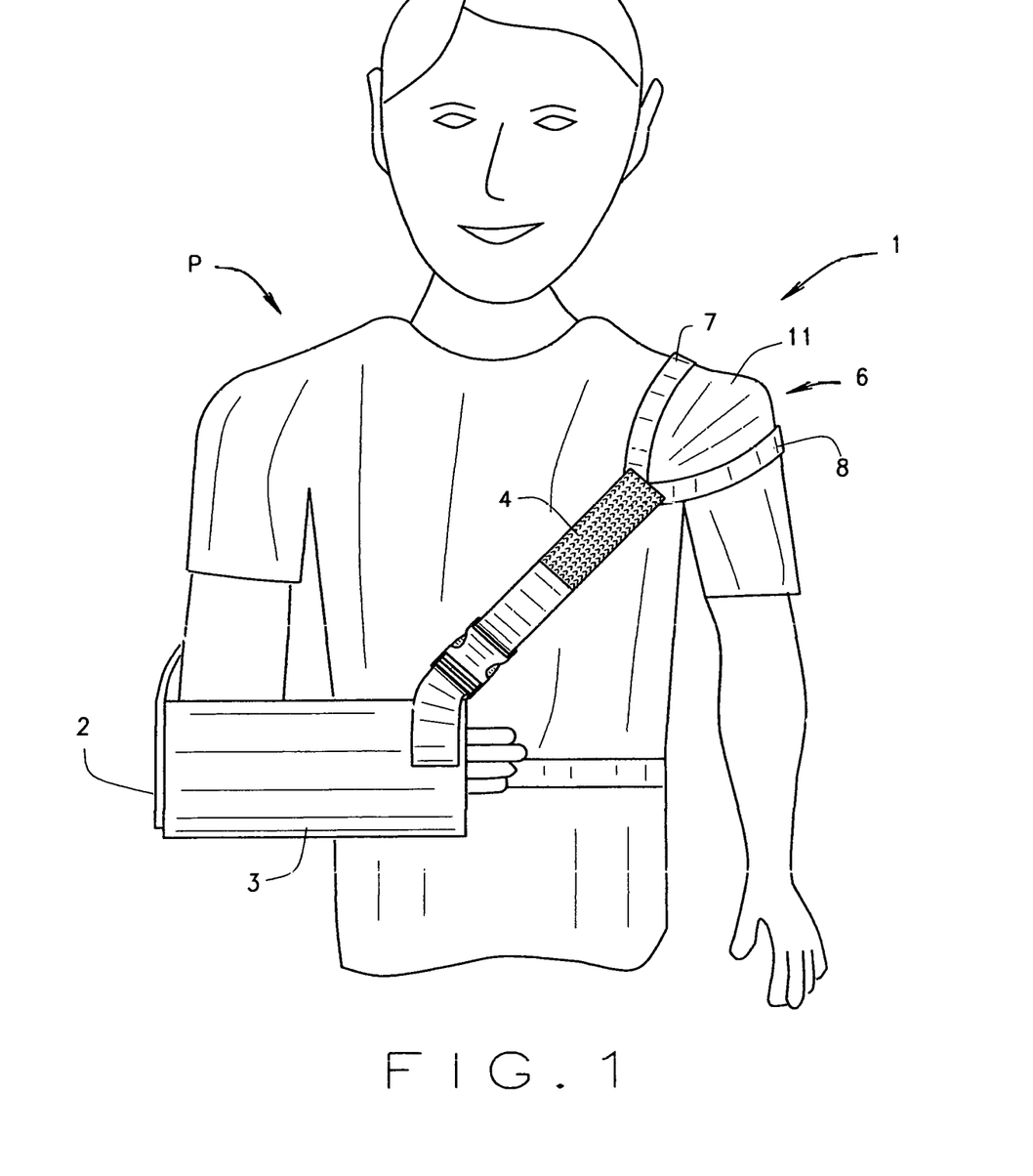
FIG. 1 is a front view of a user wearing an illustrative embodiment of the shouldered arm sling with ergonomic shoulder saddle. For all intents and purposes, it may be used in conjunction with current market devices which house an injured limb.
Figure 2:
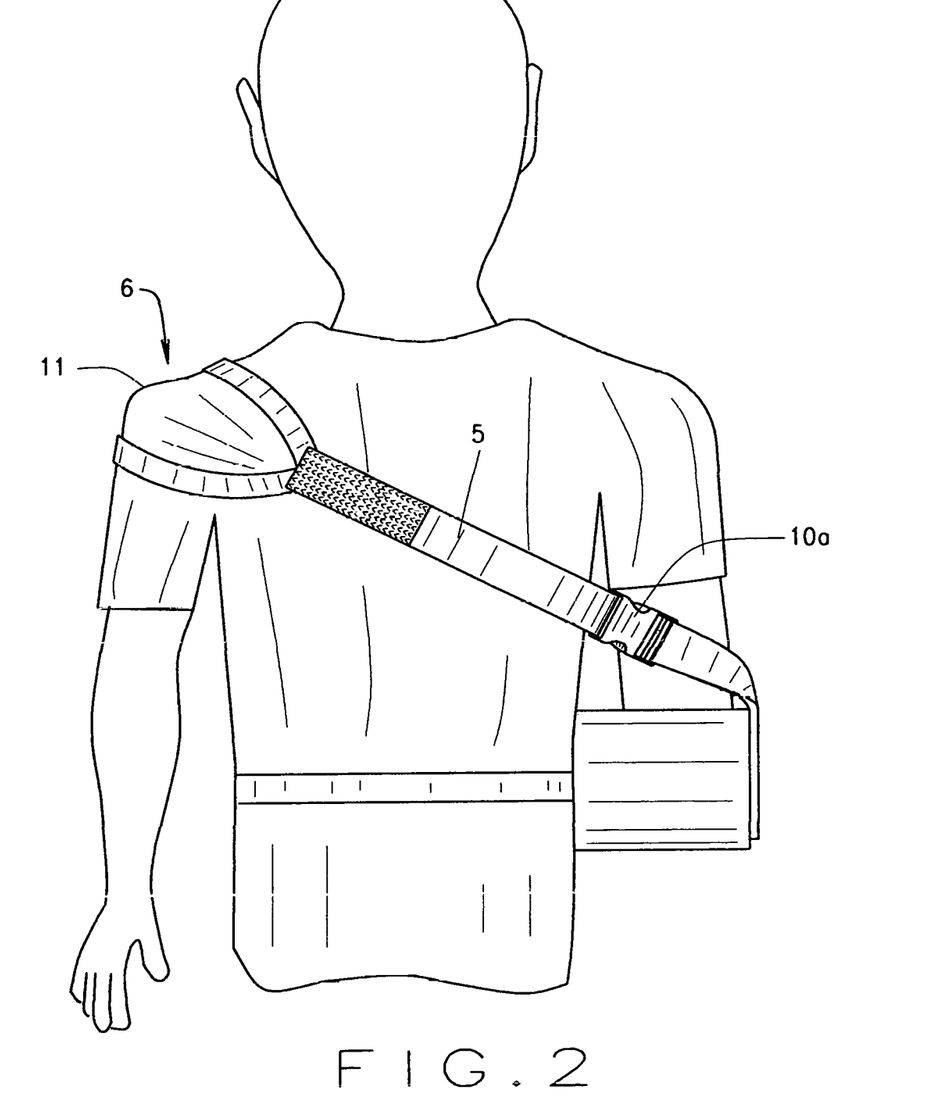
FIG. 2 is a rear view of the sling of FIG. 1.
Figure 3:
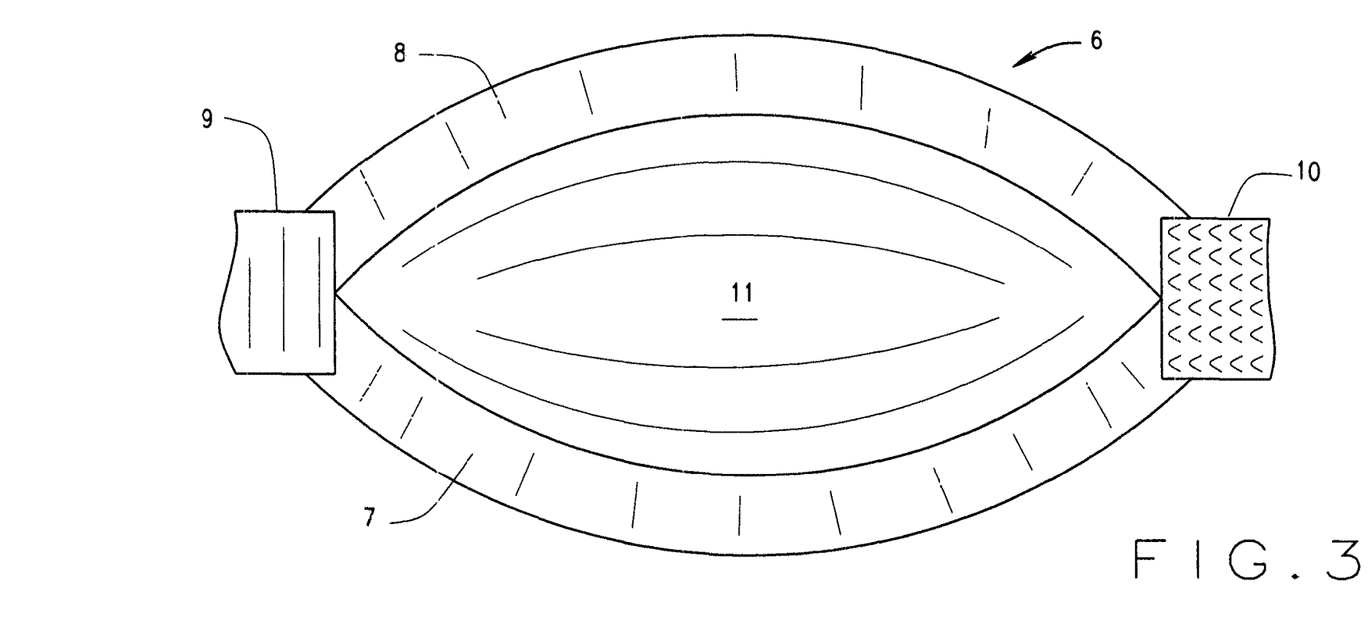
FIG. 3 is a top view of the shoulder saddle for illustrating the bifurcated strap system of this invention.

In referring to FIG. 1, the shouldered arm sling 1 of this invention is readily disclosed. It shows the sling 2, itself, and as can be seen, the sling wraps partially around the lateral waist of the patient P as can be noted at 3. The primary straps 4 and 5 (see FIG. 2) connect with the member 3 and extend upwardly for securement with the shoulder saddle 6 of this invention. As can be seen, as noted in FIG. 3, the shoulder saddle 6 includes a pair of bifurcated straps, 7 and 8, which have connectors at either end, as at 9 and 10, for securement with the primary straps 4 and 5, of the sling structure. These saddle straps may be made of any strapping material, such as fabric, or even polymer, and may even have some resiliency to them, to provide for the convenience of their settling upon the opposite shoulder of the patient, during usage. In addition, these saddle straps 7 and 8 may have some padding provided within or on them, so as to further add to the comfort of the patient during usage, and while the patient is convalescing. Further, as can be seen, there is an intermediate flexible type of fabric 11 and this fabric may be just that, a cloth fabric secured to the inner edges of the saddle straps 7 and 8, and act as a further support, as can be noted in FIGS. 1 and 2, for resting against the outer edge of the weight carrying shoulder, to help disseminate the various forces generated by the weight of the supported arm. Or this intermediate structure 11 may be formed of very resilient material, such as rubber, or resilient strands, formed into a webbing like member, so as to allow the saddle straps 7 and 8 to be further separated, in order to accommodate a larger sized shoulder of the patient during treatment.

As can be understood, the weight of the arm, within the sling 2 and 3, is transmitted up to that shoulder saddle 6, as can be noted. With that type of diagonal force, generated from the weight of the treated arm, there are various vector forces that are generated, select of which may be vertically oriented, and other forces that may be generated laterally, and these forces are usually absorbed by these two saddle straps 7 and 8, with the strap 7 absorbing some of the vertical forces, and the strap 8 absorbing the lateral forces, and with the flexible member 11 intermediate thereof, further providing support for the weight of the arm being conveyed. This is an example as to how the usage of this shoulder saddle strap 6 can help disseminate the weight of the load of the supported arm and add to the comfort of the long term usage of the sling, during the many weeks of convalescence in treating a broken arm, until it heals.

Also, the lateral strap 8 prevents the associated strap 7 from sliding up against the neck, and causing abrasion as occurs with many of the prior art slings.

Figure 4:
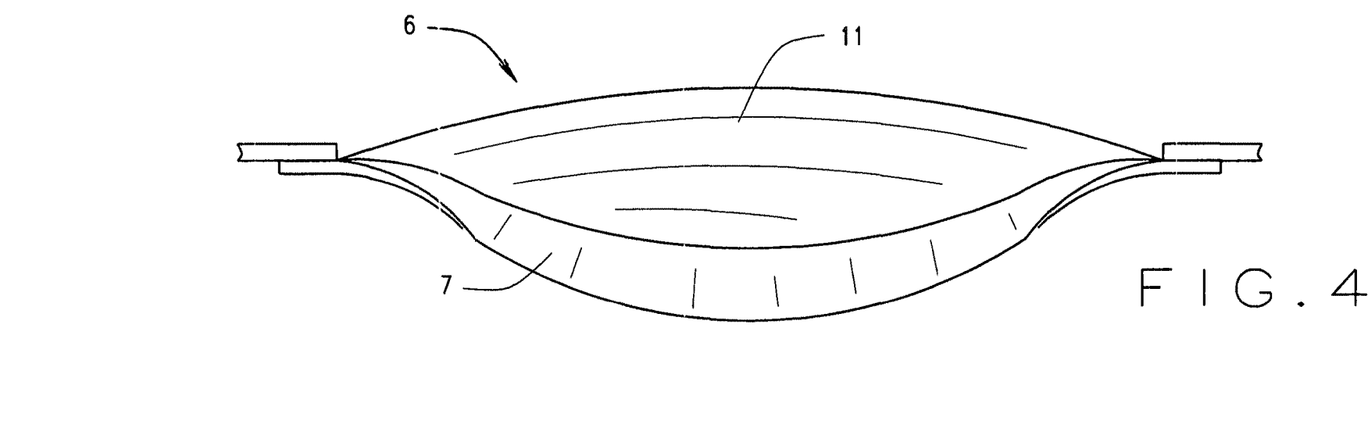
FIG. 4 is a side view of the shoulder saddle to further illustrate its concave quality.

FIG. 4 shows a side view of the saddle strap 6, and how its straps 7 and 8 may be separated, and with the intermediate flexible member 11 provided therein, forms a type of concave form of support for resting upon both the upper and lateral portions of the shoulder, to help disseminate the generated forces, all for the comfort of the patient.

Figure 5:
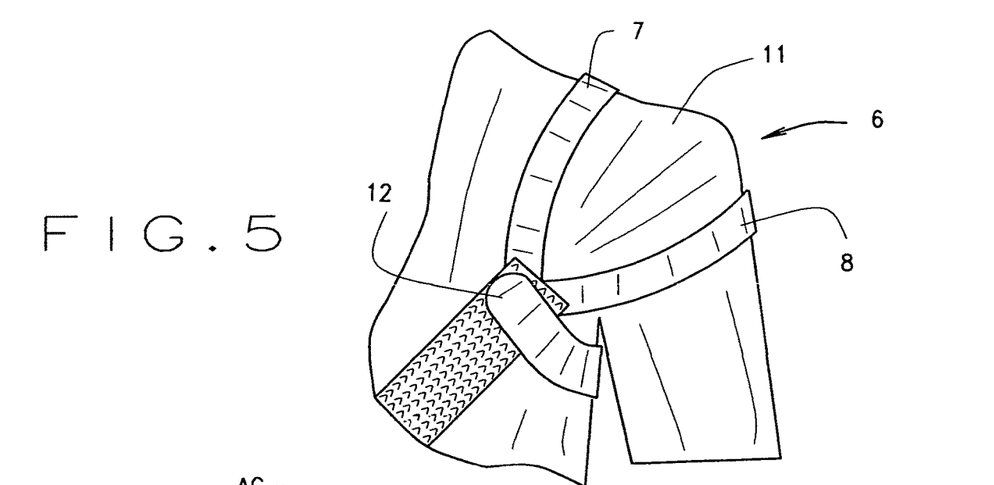
FIG. 5 is an enlarged view of a user utilizing the shoulder saddle system with a resilient mesh fabric filling the area between the bifurcation of the strap which is structured into concave form by the user's shoulder and spreads the forces in supporting the arm, and a supplemental sleeve to adhere the outermost portion of the saddle to the lower portion of the deltoid to position the saddle on the shoulders.

FIG. 5 shows the shoulder saddle strap 6 in position upon the shoulder of the patient, disclosing its straps 7 and 8, its intermediate flexible fabric 11, and a clips 10a provided at the ends of the saddle strap, for attachment with the straps 4 and 5 of the sling structure. Also disclosed is an optimal supplemental strap or sleeve 12 that causes strap 8 to adhere to the most lateral part of the deltoid, which further maintains the saddle 6 stationary and prevents its medial movement during usage.

Figure 6:
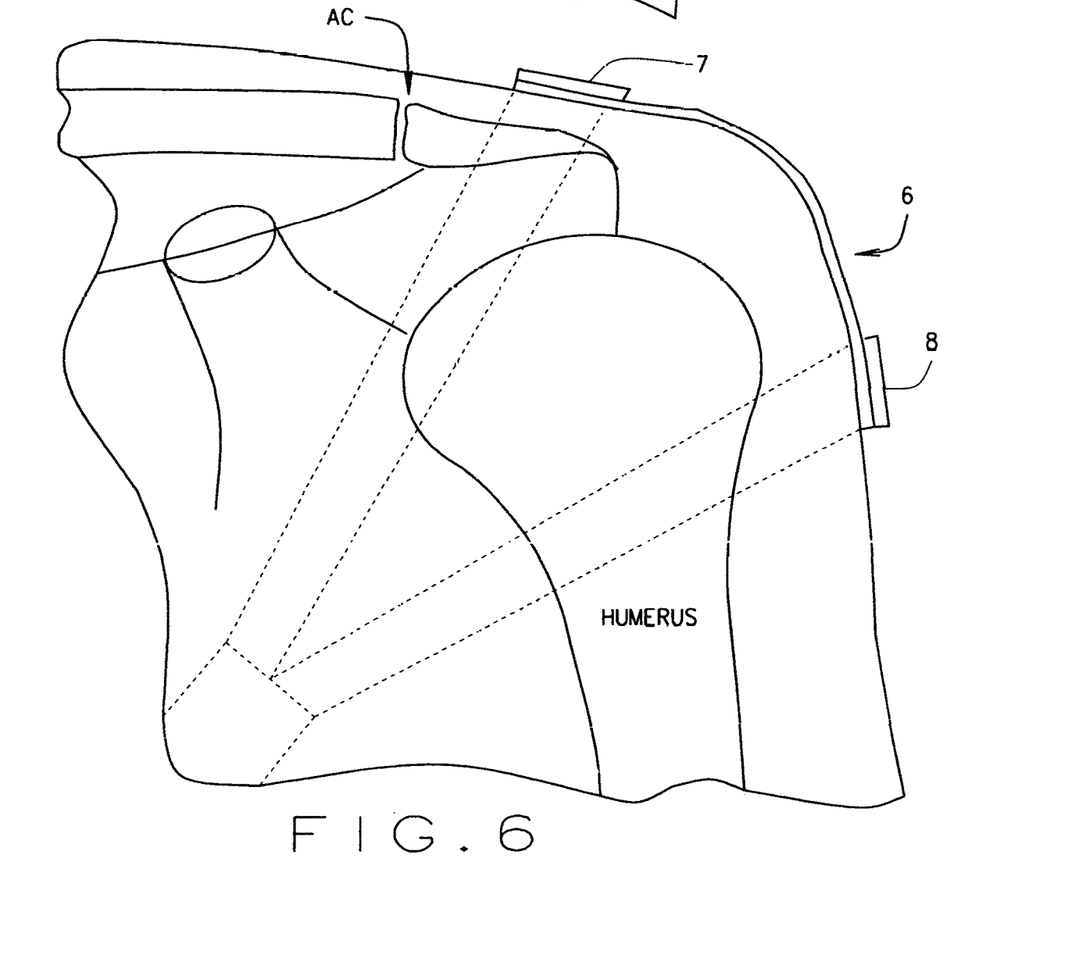
FIG. 6 is an X-ray schematic detailing how the arm sling shoulder saddle system relieves and disseminates the forces of weight on sensitive bone areas to relieve from stress, limiting applied force to only the strong deltoid area.

FIG. 6 provides a more anatomical schematic showing of the various bone structure, within the body, and how the saddle strap 6 rests on the upper outer edge of the shoulder, having its straps 7 and 8 arranged for supporting and absorbing the vector forces generated by the weight of the arm, in order to encounter and disseminate both the vertical and lateral vectoral forces generated from the weight of the arm being supported.

Figure 7:
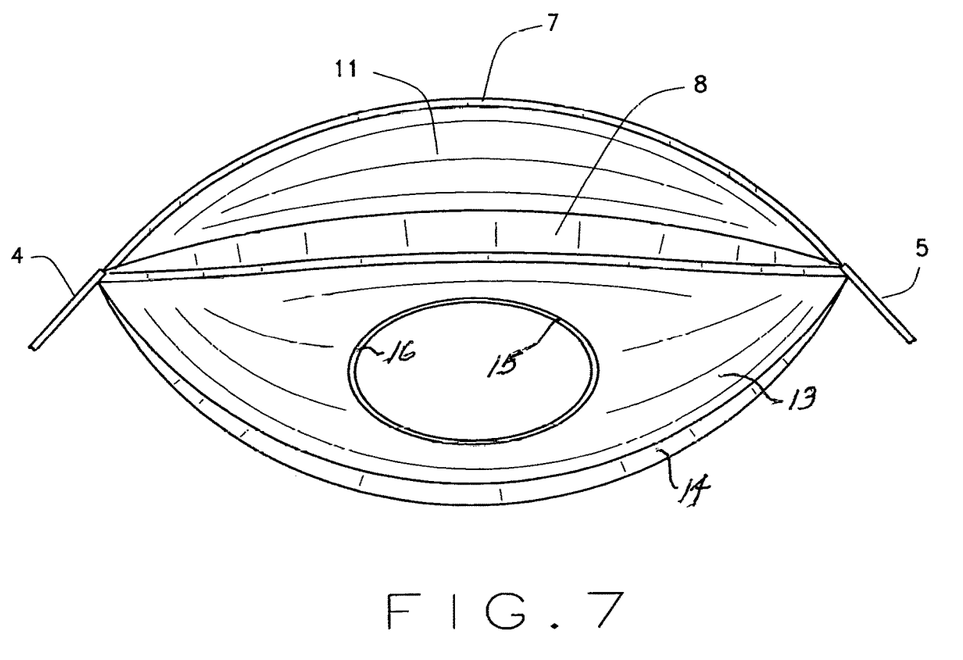
FIG. 7 provides a partial side view of the arm sling, showing the addition of an upper arm embracing flexible member through which the arm may locate, and a sturdier lower hem for also biasing against the upper torso of the wearer's body, to stabilize the securement of the sling during usage.

As disclosed in FIG. 7, a supplemental means is provided for cooperating with the upper arm of the user, in order to stabilize the locating of the arm sling in position, and to further prevent its movement towards the neck of the user, and to maintain the locating of its two saddle straps 7 and 8 as positioned upon the shoulder of the said user. As noted, the primary straps 4 and 5 connect with the saddle straps 7 and 8, as previously explained. And a flexible member 11 is provided intermediate thereof, and which functions as a means to maintain the space between the saddle straps 7 and 8, during usage, and to achieve the purposes of their provision within the structure of this shoulder arm sling. Furthermore, connecting with the outer saddle strap 8 is an additional flexible and resilient material, whether it be netting, flexible light cloth, all as noted at 13, and which includes a hem 14 at its lower region, as can be noted. Then, there is an opening, as at 15, provided through the material 13, and which also is lined around its circumference with a hem, as noted at 16, and which functions to resiliently bias against the upper arm or deltoid of the user, as the arm extends through the opening 15, this entire feature provided for holding the arm sling in its cradled position, and prevent the saddle straps 7 and 8 from migrating towards the neck of the user, when the arm is inserted therethrough, in order to avoid any abrasion at that location, and furthermore to disseminate the weight of the arm being carried, in the manner as previously described. This opening 15 may be provided close to the hem 14 to furnish more clearance for the arm. This is an additional feature of this sling, which is designed to provide and add to the comfort of the user, in addition to spread the weight of the injured arm, which might include a weighted cast, during convalescence. Also, the member 13, if not desired for usage, can be folded inwardly against and under the flexible member 11 for non-usage.

Figure 8:
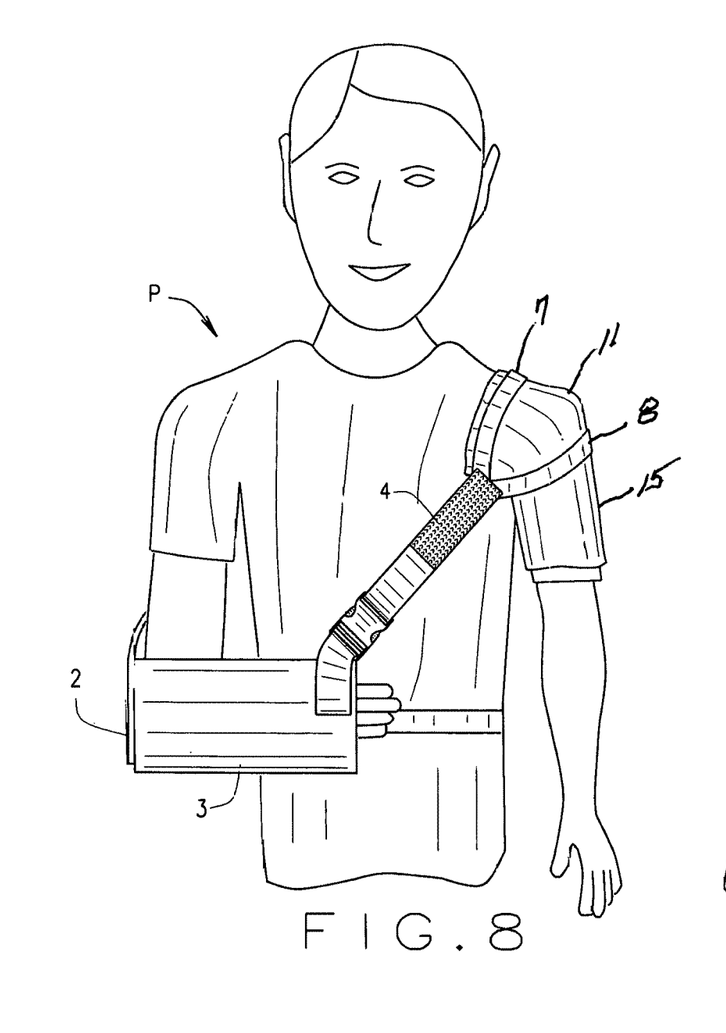
FIG. 8 is a front view of a modification to the arm sling that can support the open arm during its convalescence, and prevent the rise up of the shoulder saddle during its usage and applications.
Figure 9:
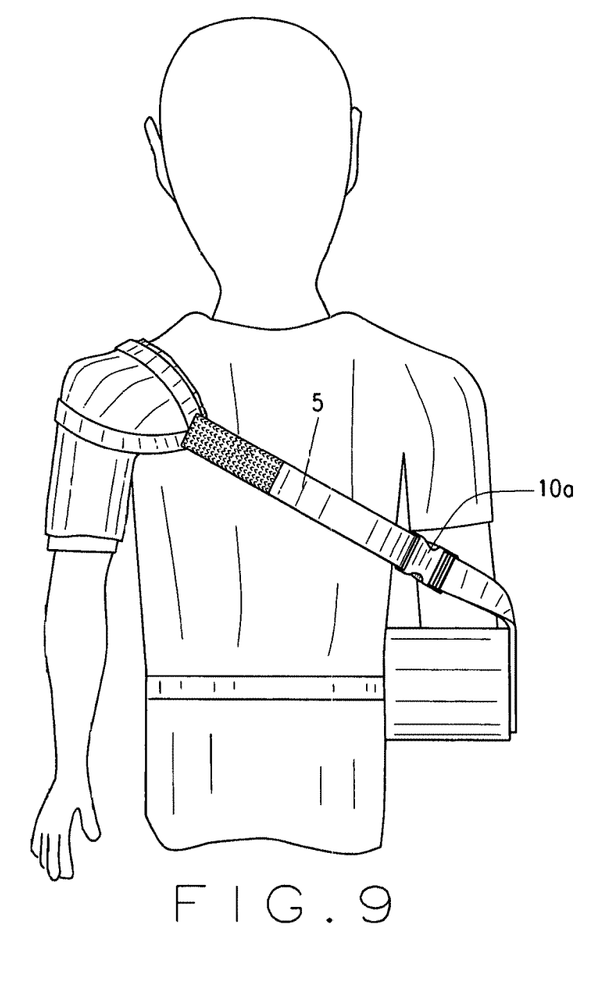
FIG. 9 is a back view of the modified arm sling of this invention.

As can be seen in FIGS. 8 and 9, a modification to the shouldered arm sling can be seen. Generally, the arm sling is very similar in construction to that as previously reviewed and identified in this application. But, the addition is to provide means to prevent the rising up onto the shoulder of the straps 7 and 8, and which may also have the flexible member 11 provided intermediate thereof, but in this instance, a short length of sleeve 15 is affixed to the strap 8, and embraces the bicep of the arm of the wearer, and thereby prevents a rising up of the straps 7 and 8, or its flexible member 11, and to prevent them from abrading the upper shoulder or neck portion of the wearer, during convalescence. There is related strapping as at 4 and 5 to hold the sling in place, and connecting with the straps 7 and 8, as can be noted. The sleeve 15 embraces the bicep, and holds the straps 7 and 8 from sliding further upwardly, during their application, and wearing of the shouldered arm sling during usage.

It is to be noted that various fasteners such as buckles, stitching, and hooks and pile fastening means (Velcro) can be utilized to hold these various sling components together, during usage.

Variations or modifications of the subject matter of this invention may occur to those skilled in the art upon review of disclose as provided herein. Such variations, within the spirit of this invention, are intended to be encompassed within the scope of any claims to patent protection to be obtained. The description of the invention as set forth herein, and as shown in the drawings, are intended to be set forth for illustrative purposes only.

The invention claimed is:

1. An arm sling assembly adapted for supporting an injured arm of a user, the arm sling assembly comprising:
   a sling configured for wrapping under the injured arm of the user;
   an anterior strap connected to a first end of the sling and configured to extend from the first end of the sling upwardly and diagonally across an anterior of the user to a shoulder of an opposite, uninjured arm of the user;
   a posterior strap connected to a second end of the sling and configured to extend from the second end of the sling upwardly and diagonally across a posterior of the user to the shoulder of the opposite, uninjured arm of the user;
   a shoulder saddle adapted to conform to the shoulder of the opposite, uninjured arm of the user, the shoulder saddle having a first strap having opposite ends connected between the anterior strap and the posterior strap and a second strap having opposite ends connected between the anterior strap and the posterior strap, the first strap being adapted to engage on an upper portion of the shoulder of the opposite, uninjured arm of the user, the second strap being adapted to engage on a lateral portion of the shoulder of the opposite, uninjured arm of the user, whereby a weight of the injured arm of the user is disseminated over the shoulder of the opposite, uninjured arm of the user; and
   the shoulder saddle further comprising the first strap and the second strap connected with an intermediate flexible fabric positioned between the first strap and the second strap whereby the intermediate flexible fabric is configured to form a concave structure adapted for resting on the shoulder of the opposite, uninjured arm of the user and a supplemental strap connected to the first strap and the second strap and extending under the opposite, uninjured arm of the user, the supplemental strap is configured to maintain the second strap engaged on the lateral portion of the shoulder of the opposite, uninjured arm of the user and maintain the shoulder saddle stationary and prevent medial movement of the shoulder saddle.

2. The arm sling assembly of claim 1, further comprising:
   padding on the first strap configured to engage on the upper portion of the shoulder of the opposite, uninjured arm of the user; and
   padding on the second strap configured to engage on the lateral portion of the shoulder of the opposite, uninjured arm of the user.

3. The arm sling assembly of claim 1, further comprising:
   the intermediate flexible fabric positioned between the first strap and the second strap being formed of one of resilient cloth, rubber or resilient strands.

4. The arm sling assembly of claim 1, further comprising:
   the first strap and the second strap being constructed of strapping material.

5. The arm sling assembly of claim 1, further comprising:
   fasteners securing components of the arm sling assembly together, the fasteners comprising buckles, stitching, and hook and pile fastening means.

6. The arm sling assembly of claim 5, further comprising:
a sleeve secured to the shoulder saddle, the sleeve being adapted to receive the opposite, uninjured arm of the user in the sleeve and prevent movement of the shoulder saddle.

7. The arm sling assembly of claim 5, further comprising:
a flexible member secured to the second strap, the flexible member having a lower hem reinforcing the flexible member, the flexible member having an opening through the flexible member adapted for insertion of the opposite, uninjured arm of the user through the opening.

8. The arm sling assembly of claim 1, further comprising:
a sleeve affixed to the second strap, the sleeve being adapted to receive the opposite, uninjured arm of the user in the sleeve and prevent movement of the first and second straps on the shoulder of the opposite, uninjured arm of the user.

\* \* \* \* \*